(12) United States Patent
Huff et al.

(10) Patent No.: US 8,252,002 B2
(45) Date of Patent: Aug. 28, 2012

(54) MODULAR TRIAL MECHANISM

(75) Inventors: Daniel N Huff, Warsaw, IN (US); Larry G McCleary, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 383 days.

(21) Appl. No.: 12/609,594

(22) Filed: Oct. 30, 2009

(65) Prior Publication Data
US 2011/0106270 A1 May 5, 2011

(51) Int. Cl.
*A61B 17/58* (2006.01)
*A61B 17/72* (2006.01)

(52) U.S. Cl. .......................................... 606/102; 606/62
(58) Field of Classification Search .................. 606/62; 403/409.1
See application file for complete search history.

(56) References Cited

U.S. PATENT DOCUMENTS

| | | | |
|---|---|---|---|
| 5,100,407 A | 3/1992 | Conrad et al. | |
| 5,352,227 A * | 10/1994 | O'Hara | 606/63 |
| 5,590,975 A * | 1/1997 | Horntvedt | 403/320 |
| 5,601,567 A | 2/1997 | Swajger et al. | |
| 5,620,445 A * | 4/1997 | Brosnahan et al. | 606/63 |
| 5,645,607 A | 7/1997 | Hickey | |
| 5,888,208 A | 3/1999 | Ro | |
| 6,126,694 A | 10/2000 | Gray, Jr. | |
| 6,193,759 B1 | 2/2001 | Ro et al. | |
| 6,395,004 B1 | 5/2002 | Dye et al. | |
| 6,432,110 B1 | 8/2002 | Richelsoph | |
| 7,273,499 B2 | 9/2007 | McCleary et al. | |
| 2003/0204262 A1 | 10/2003 | Ferguson | |

FOREIGN PATENT DOCUMENTS

| | | |
|---|---|---|
| EP | 0163121 A1 | 12/1985 |
| EP | 0767638 B1 | 7/1999 |
| EP | 1639963 A1 | 3/2006 |
| WO | WO 01/82843 A2 | 11/2001 |

OTHER PUBLICATIONS

European Search Report for Corresponding EPO Application No. 10187325.5-2310 Dated Feb. 25, 2011, 7 Pages.

* cited by examiner

*Primary Examiner* — Nicholas Woodall (57) ABSTRACT

A prosthetic trial for a joint prosthesis includes a stem having a proximal section and a distal section for implantation in a bone. A body includes a channel receiving at least the proximal section of the stem. A locking mechanism is at least partially disposed within the body. The locking mechanism is biased into a locking position in which the mechanism locks the stem within the first channel of the body. The locking mechanism is accessible outside said body to be pulled into a releasing position to unlock the stem from the body.

12 Claims, 6 Drawing Sheets

MODULAR TRIAL MECHANISM

TECHNICAL FIELD OF THE INVENTION

The present invention relates generally to a surgical trial instrument assembly and, more particularly, to a surgical trial instrument assembly for determining the required dimensions of a prosthetic femoral component.

BACKGROUND OF THE INVENTION

During the lifetime of a patient, it may be necessary to perform a joint replacement procedure or arthroplasty on the patient as a result of, for example, disease or trauma. One such type of joint replacement procedure is a hip replacement procedure in which a diseased and/or damaged hip joint is replaced with a prosthetic hip joint. A typical hip replacement procedure utilizes a prosthesis that generally includes a femoral stem component, a proximal body component, and a neck segment. The femoral stem is implanted in a prepared medullary canal of the patient's femur.

During performance of such a hip replacement procedure, the surgeon must evaluate the size and condition of the patient's bones (e.g. the patient's femur) in order to determine the proper type and configuration of each of the various types of prosthetic components that are to be implanted. One or more provisional components are temporarily fixed to a bone prior to permanent fixation of the prosthetic joint. The provisional components are intended to mimic certain aspects of the permanent prosthetic joint in order for a surgeon to validate measurements and to test several different possible component sizes and shapes. Hence, provisional components are aptly known as "trials", and the procedure is known as "trialing."

Currently, in a majority of revision total hip arthroplasties, the bone has little or no supportive metaphysis or diaphyseal areas. This makes it difficult for surgeons to reproduce the proper anatomy. To do this, the surgeon may use a distally fixed implant. This facilitates trialing from the distal femoral cortex and subsequent proximal anatomy. Many trials are used in surgery having one basic anterior/posterior proximal anatomical body with altering characteristics (i.e., stem lengths, bow, offsets, neck lengths, neck anteversion). Each instance requires a single monolithic trial that duplicates the implant, which is therein made from casting substrate. Some trialing techniques utilize the broach as the stem and then attach a proximal trial onto the broach.

Other techniques require that the broach be removed from the medullary canal to allow the use of a trial having a stem portion, a head and a neck. For example, some have disclosed a system including a group of variously sized trial neck/body portions and a group of differing length trial stem portions which are mixed and matched to create a suitable trial. The trials are held together using a ball and spring detent system. Such ball and spring systems do not create a tight, wiggle-free connection. Because the trial pieces are not held tightly together, there can be errors in the use of the actual implant.

Because many variations in sizes and shapes of trials are required to be available to the surgeon, it is necessary to maintain a large inventory of trials. Such a large inventory is costly, occupies valuable operating room space, and is difficult to manage. If the trial is a singular piece, then there must be upwards of 50 full trials. These full trials take up large amounts of space in instrument sets.

In some modular trials, the different parts of the trial are assembled using threads. However, this makes connection and disconnection lengthy and cumbersome. In other modular trial designs, the different parts are held together by nothing more than a ball plunger of balseal. These features are not suitable for a solid, wiggle-free connection which resists tensile forces as well as rotational ones. Others use the reamer as the trial stem. However, not all distal reamers are suitable for working as trials.

SUMMARY OF THE INVENTION

According to one embodiment of the present invention, a modular prosthetic trial for a joint prosthesis. The trial includes a first piece having a proximal section and a distal section configured for implantation in a bone. The proximal section includes a non-threaded proximally extending protrusion. The trial also includes a second piece having a proximal section and a distal section, the distal section including a recess for receiving the non-threaded proximally extending protrusion. A locking mechanism is at least partially disposed within the recess of the second piece. The locking mechanism is sized and shaped to engage the protrusion such that the locking mechanism locks the first piece to the second piece.

According to another embodiment of the present invention, a method for assembling a modular trial is provided. The method includes inserting a non-threaded proximally extending protrusion from a first piece into a corresponding recess in a distal portion of a second piece. The proximally extending protrusion engages a locking mechanism disposed in the second piece. The method further includes activating the locking mechanism to lock the first piece to the second piece.

According to yet another embodiment of the present invention, a kit for use in performing joint arthroplasty is provided. The includes a plurality of first trial pieces having a proximal section and a distal section configured for implantation in a bone. The proximal section has a non-threaded proximally extending protrusion. The kit also includes a plurality of second trial pieces having a proximal section and a distal section. The distal section includes a recess for receiving the non-threaded proximally extending protrusion and the proximal section includes a non-threaded proximally extending protrusion. Each of the plurality of second trial pieces includes a locking mechanism at least partially disposed within the recess of the second trial piece. The locking mechanism is sized and shaped to engage the protrusion such that the locking mechanism locks the first trial piece to the second trial piece. The kit also includes a third trial piece that includes a proximal end and a distal end. The distal end includes a recess for receiving the non-threaded proximally extending protrusion of one of the plurality of second trial pieces, and the distal end includes a locking mechanism at least partially disposed within the recess of the third trial piece. The locking mechanism is sized and shaped to engage the protrusion such that the locking mechanism locks the second trial piece to the third trial piece.

The above and other features and advantages of the present invention will become apparent from the following description and the attached drawings.

DETAILED DESCRIPTION OF THE INVENTION

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

It should initially be appreciated that the present invention can be used after proper resection of a patient's proximal femur for evaluating the size and shape of an implant therefor prior to committing to the final preparation of the proximal femur. The proximal end portion of the patient's femur can be resected by use of, for example, a bone saw (not shown). Proper resection of the proximal femur is beyond the scope of the present disclosure. Reference should be made to an appropriate surgical manual for such resection.

Figure 1:
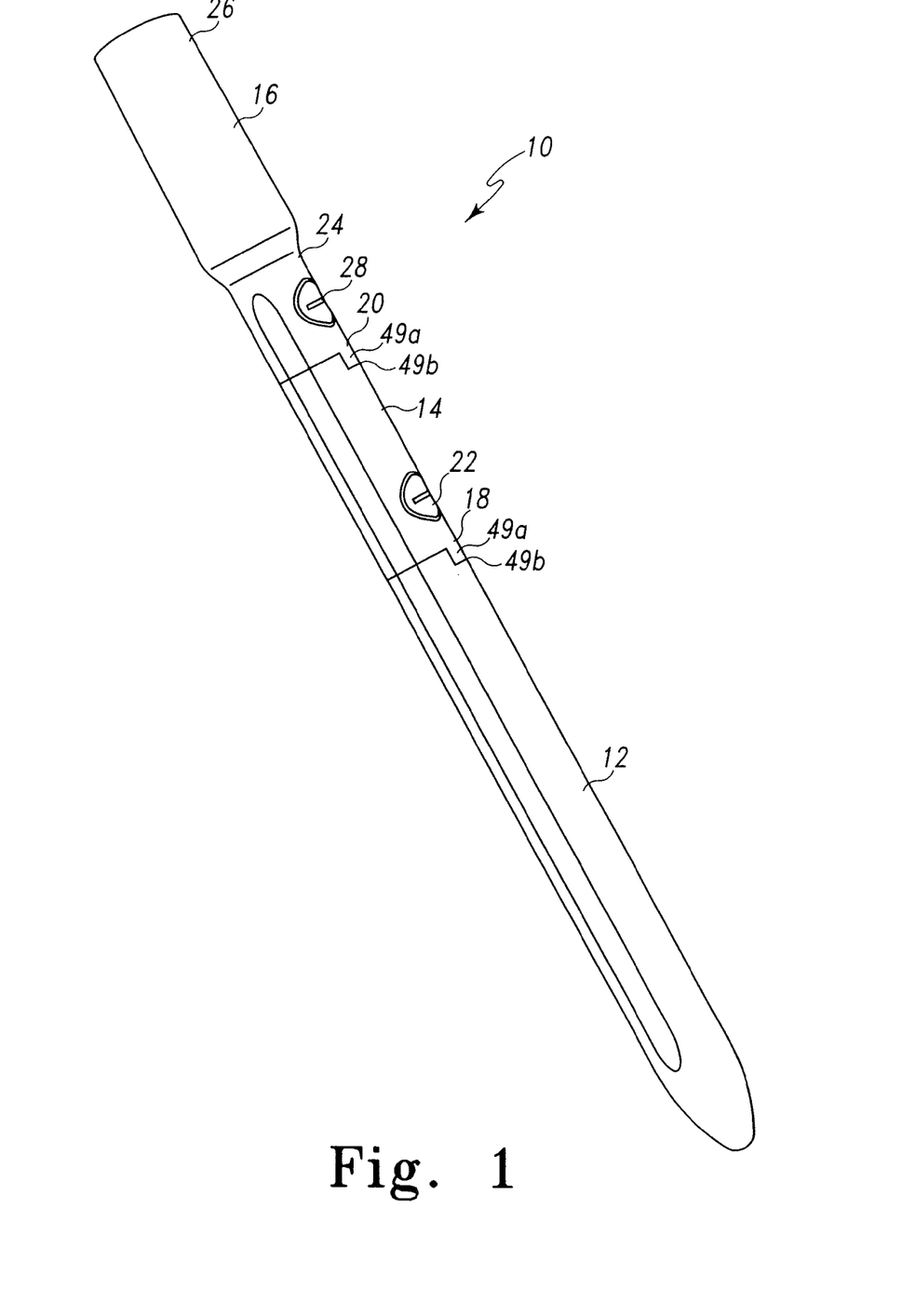
FIG. 1 illustrates a perspective view of a modular trial assembly according to one aspect of the present invention.

Referring now to FIG. 1, there is shown a modular trial assembly 10 according to one embodiment of the invention, including a first piece or distal body 12, a second piece or middle body 14, and a third piece or proximal body 16. In this embodiment, each of the pieces makes up part of a distal stem. However, it should be appreciated that in other embodiments, the pieces may make up different parts of a different implant or trial.

As shown in FIG. 1, the middle body 14 includes a distal section 18 and a proximal section 20. The distal section 18 includes a locking mechanism 22. The proximal body 16 also includes a distal section 24 and a proximal section 26. The distal section 24 of the proximal body 16 also includes a locking mechanism 28.

Figure 2:
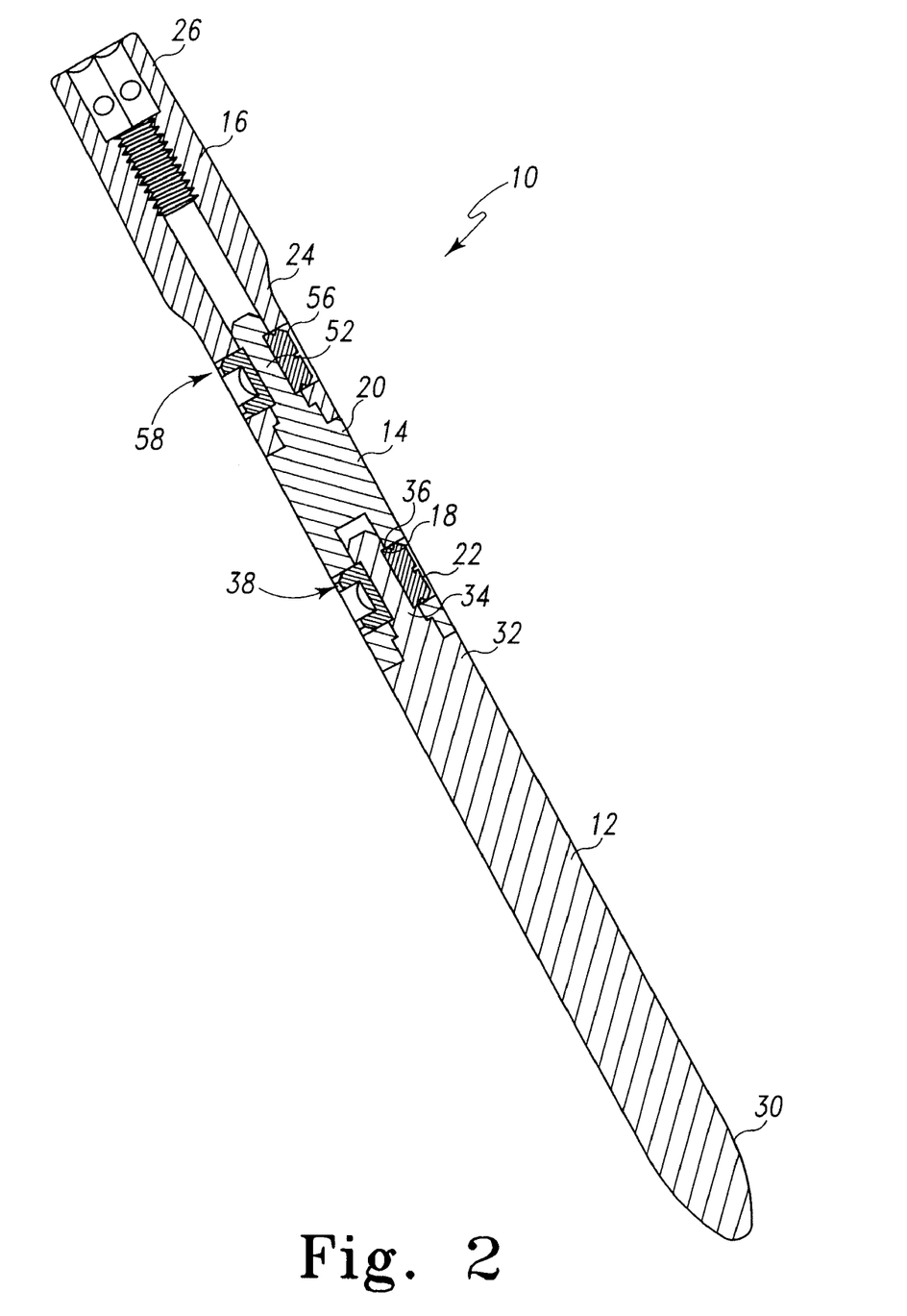
FIG. 2 illustrates a partially cut-away view of the modular trial assembly of FIG. 1.

FIG. 2 shows a cross-sectional view of the modular trial 10. As shown, the distal body 12 has a distal section 30 that is configured for implantation into a bone. The distal body 12 also has a proximal section 32. The proximal section 32 includes a non-threaded proximally extending protrusion 34, which in the illustrated embodiment is a pin. In this embodiment, the pin includes a lip 36. In other embodiments, other types of protrusions may be used. Also, other types of shapes other than lips may be used.

As shown in FIG. 2, the pin 34 extends into a recess 38 of the middle body 14. The locking mechanism 22 of the middle body 14 is also at least partially disposed in the recess 38. As shown, the locking mechanism 22 engages the lip 36 of the pin 34.

Figure 3:
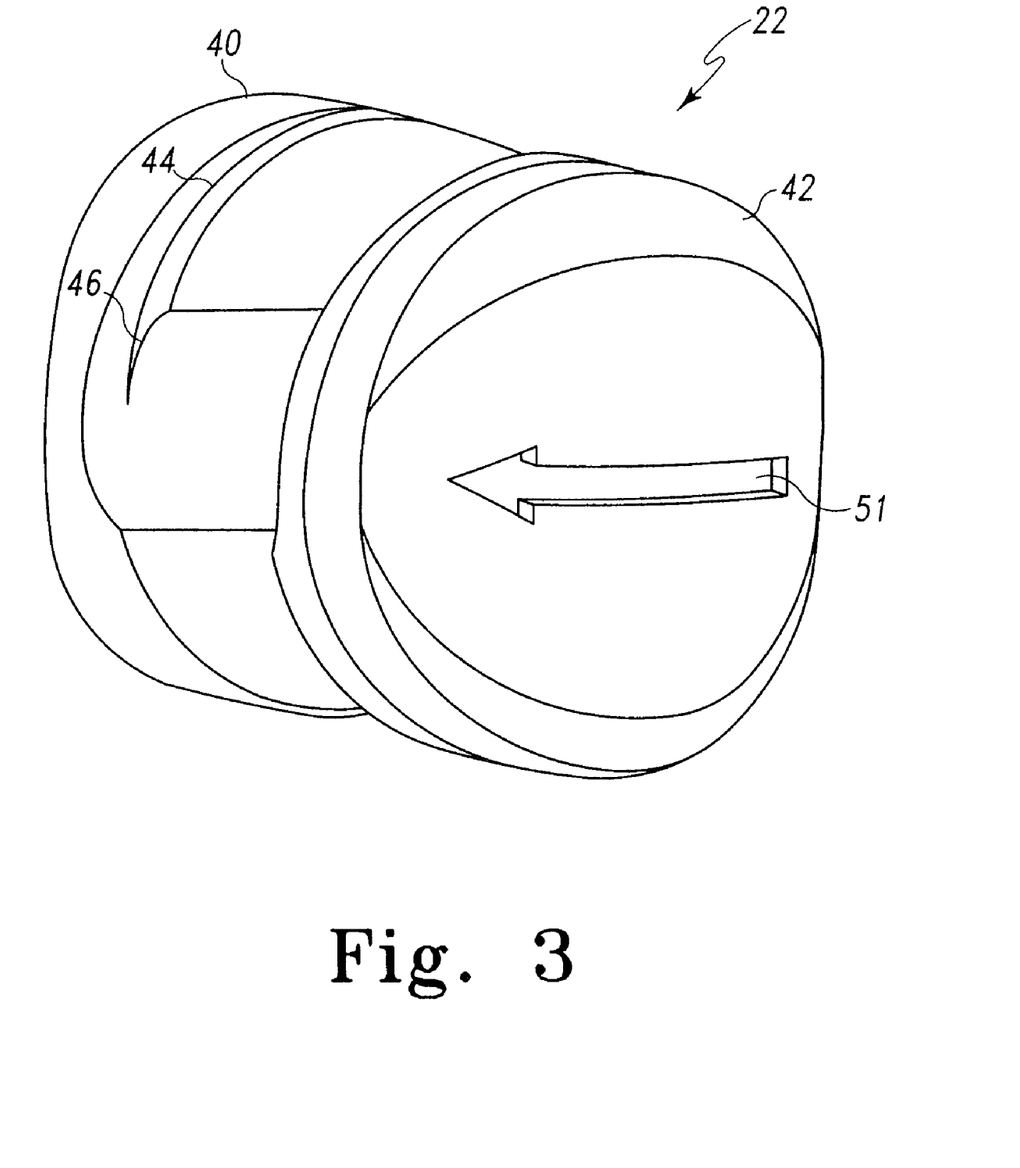
FIG. 3 is a perspective view of a locking mechanism according to one embodiment of the present invention.

Turning now to FIG. 3, a perspective view of the locking mechanism 22 is shown. The locking mechanism 22 includes a first wall 40 and a second wall 42 opposite the first wall 40. The first and second wall 40, 42, each define an interior groove or recess 44 that is sized and shaped to receive the pin 34. At an end of the groove 44, the wall 40, 42 forms a spiral-shaped edge 46. The spiral shaped edge 46 gradually spirals toward an edge of the wall 40, 42. Although in FIG. 3, only one edge 46 is shown, it should be understood that the edge 46 may be formed in both walls 40, 42. Although in other embodiments, the edge 46 may only be formed in one of the two walls 40, 42. In other embodiments, the edge 46 may be cam-shaped. Alternatively, the edge 46 may be ramp-shaped.

Figure 4:
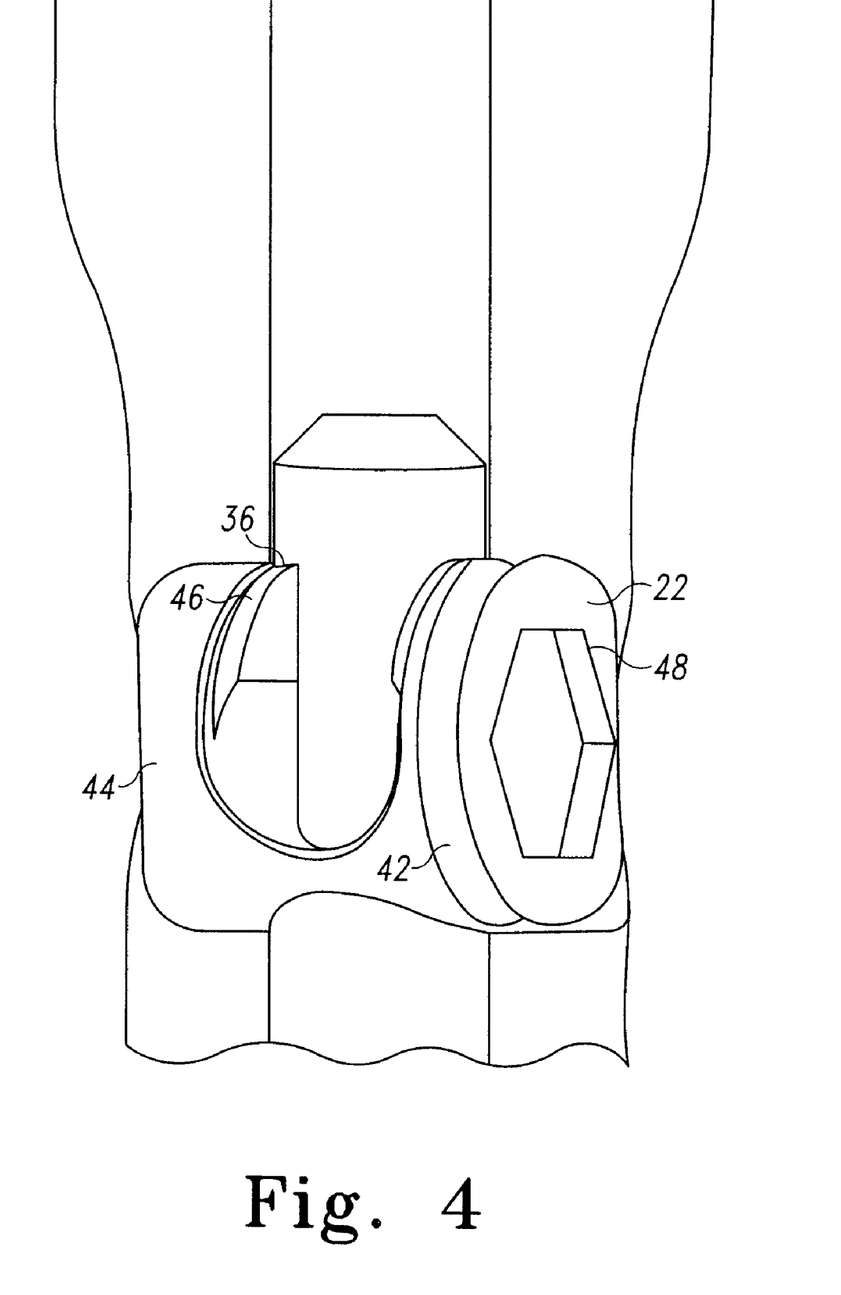
FIG. 4 is a close-up view of the modular trial assembly of FIG. 1.

As shown in FIG. 4, the edge 46 engages the lip 36. The wall 40 includes a hex-shaped recess 48 for engaging a tool (not shown). The tool engages the recess 48 and works to turn the locking mechanism 22 from an unlocked to a locked position. When the locking mechanism 22 is in the unlocked position, the pin 34 fits within the groove 44. As the locking mechanism 22 is turned, the lip 36 of the pin 34 engages the spiral edge 46. Because the edge 46 is spiral-shaped, the lip 36 rides along the edge 46 and is pulled closer to the edge of the wall 40, 42, pulling the pin 34 further into the recess 38. Once the locking mechanism 22 has been fully turned (in this case, ¼ turn) the pin 34 is locked into the recess 38.

In some embodiments, the pin 34 has two lips 36, opposing one another (not shown). In those embodiments, the locking mechanism 22 has two spiral-shaped edges 46, one for engaging each lip. As the locking mechanism 22 is turned, the lips 36 ride along the spiral edges 46, both toward the opposite edges of the walls 40, 42. This effectively locks the pin 34 in place.

As shown in FIG. 1, the distal section 18 of the middle body 14 includes at least one anti-rotation protrusion (or device) 49a. The anti-rotation protrusion 49a couples with an anti-rotation recess 49b on the proximal section of the distal body 12. The anti-rotation device and recess 49a, 49b, keep the distal body 12 and middle body 14 from rotating relative to one another. In some embodiments, there are two anti-rotation devices and recesses 49a, 49b—one on each side of the respective body 14, 12. The anti-rotation devices 49a may be of different sizes (as will be the anti-rotation recesses 49b) as this ensures that the distal body 12 will be inserted into the middle body 14 in the proper orientation. In some cases, the distal body 12 may be so slightly bowed that it is difficult to recognize. The different sized anti-rotation devices and recesses 49a, 49b ensure that the bow is correctly positioned. In the described embodiment, the middle body 14 includes a protrusion and the distal body includes a recess. Other anti-rotation devices may be used. Also, the middle body 14 may include a recess and the distal body 12 the protrusion. The connection between the proximal body 16 and the middle body 14 may also include anti-rotation devices 49a, 49b as illustrated. Other anti-rotation devices may also be used.

Returning now to FIG. 3, the wall 42 is shown with indicia 51. The indicia 51 are used to indicate when the locking mechanism is locked. In this embodiment, the indicium 51 is an arrow. When the arrow 51 points one way, the locking mechanism 22 is unlocked. When it points in a different direction, the locking mechanism 22 is locked. In some embodiments, the walls 40, 42 may also have an irregularly curved outer shape. Thus, when the locking mechanism 22 is unlocked, the outer portion of the walls 40, 42 extend out past a side of the middle body 14. When the locking mechanism 22 is in a locked position, the outer portions of the walls 40, 42 are flush with the side of the middle body 14, allowing the trial 10 to replicate an implant. In some embodiments, both indicia 51 and a curved shape may be used. In other embodiments, other indicating methods or no indicating methods may be used.

Returning now to FIGS. 1 and 2, it is shown that the proximal section 20 of the middle body 14 includes a non-threaded proximally extending protrusion 52. In this embodiment, the non-threaded proximally extending protrusion 52 of the middle body 14 is a pin—in fact, the same as the pin 34 of the distal body. The distal section 24 of the proximal body 16 includes a recess 54 and a locking mechanism 56. The recess 54 and locking mechanism 56 are the same as the recess 38 and locking mechanism 22 of the middle body 14.

Figure 5:
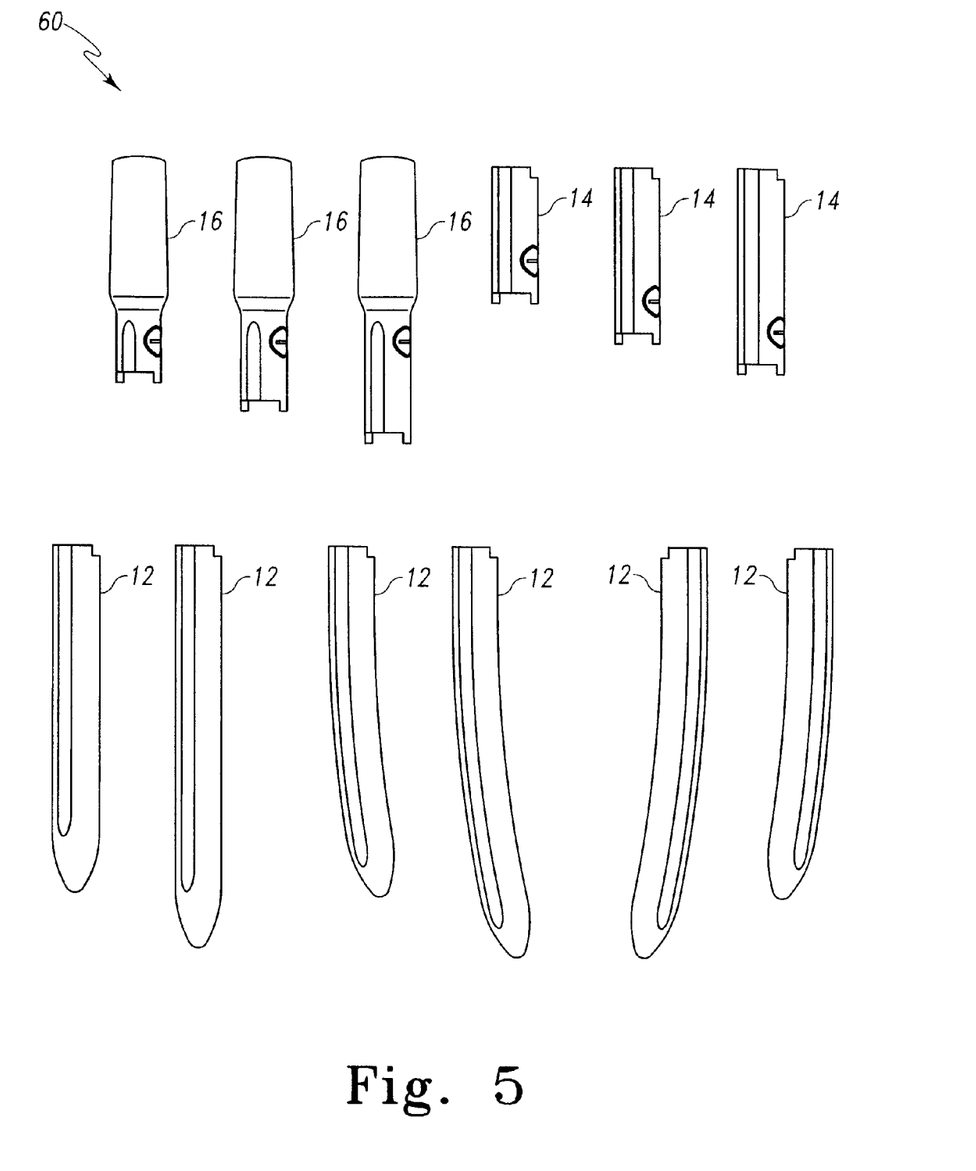
FIG. 5 illustrates a kit of a plurality of modular trial assembly parts according to one embodiment of the present invention.

Turning now to FIG. 5, a trial system kit 60 is shown according to one embodiment of the present invention. The trial system kit 60 can include multiple sizes of each of the distal body 12, the middle body 14, and the proximal body 16. In some embodiments, there may be only one proximal body 16. As shown, the multiple sizes of the distal body 12 can include different lengths and different shapes. Some of the distal bodies 12, middle bodies 14, and proximal bodies 16 include straight distal portions while others have curved or bowed distal portions. Thus, different sizes and shapes of the distal body 12, middle body 14, and proximal body 16 can be mixed and matched with one another to produce a modular trial assembly 10 (FIG. 1) that matches the size and shape of the patient's joint anatomy. Various trial assemblies may be tried in order to ascertain which final implant will work best, in the surgeon's judgment. Regardless of which combination of distal body 12, middle body 14, and proximal body 16 is used to assemble the modular trial 10, the manner of assembly, which will be discussed in detail herein, is substantially the same.

Figure 6:
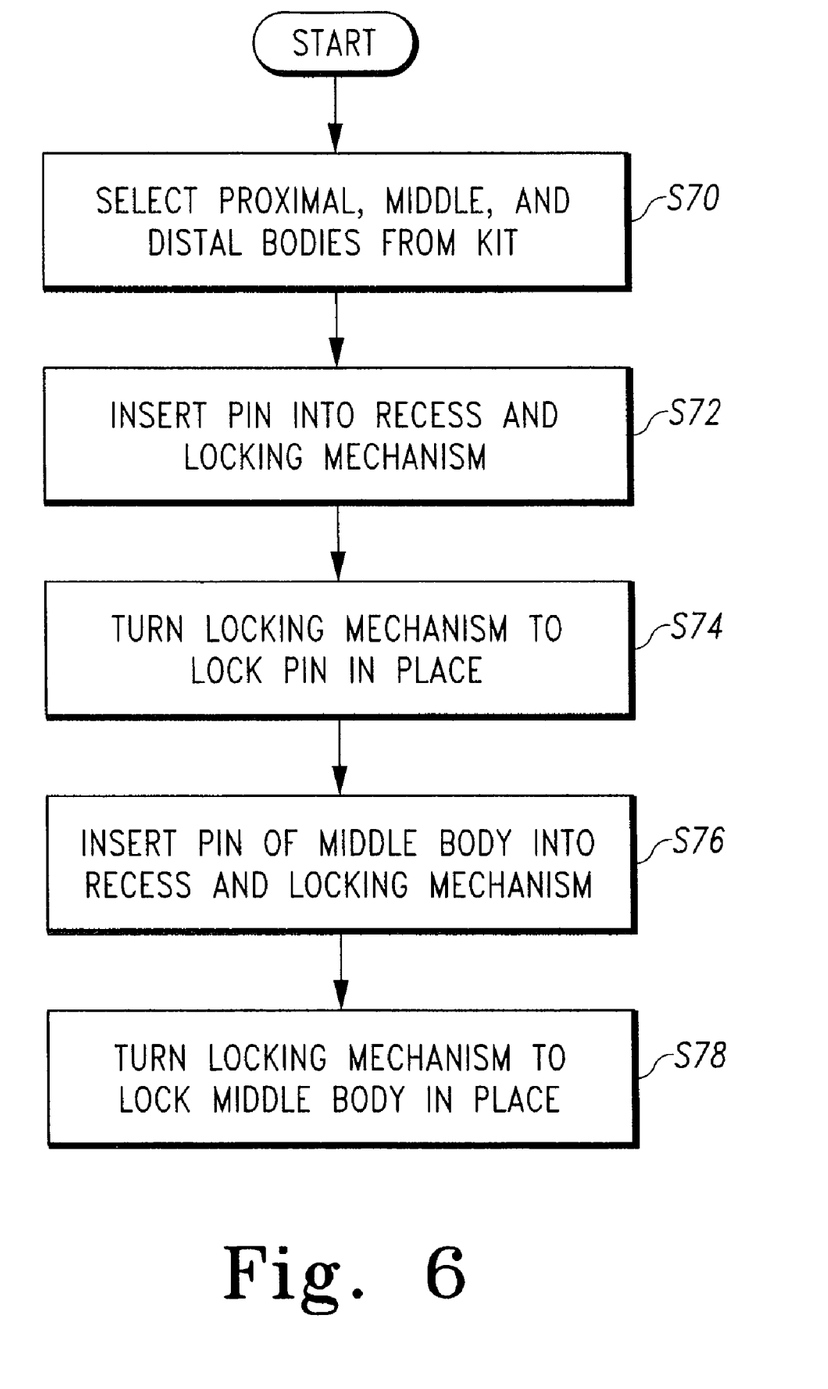
FIG. 6 is a flow chart illustrating the method of assembling a modular trial assembly according to one embodiment of the present invention.

Turning now to FIG. 6, a method for assembling the trial 10 will be described. At step s70, a distal body 12, a middle body 14, and a proximal body 16 will be selected from the kit 60. The distal body 12, middle body 14, and proximal body 16 selected will be sized and shaped such that when they are connected, the trial will match the patient's anatomy. At step s72, the pin 34 of the distal body 12 will be inserted into the recess 38 of the middle body 14 and locking mechanism 22. The locking mechanism 22 will be turned to lock the pin 34 into place (step s74). The user may decide to check using the indicia or other features (such as the shape of the locking mechanism 22) that the locking mechanism is fully locked. At step s76, the pin 52 of the middle body is inserted into the recess 54 of the proximal body 16 and locking mechanism 56. The locking mechanism 56 is then turned to lock the pin 52 in place (step s78). As before with the locking mechanism 22, the user may wish to check the indicia or other features to ensure that the locking mechanism 56 is locked. The trial 10 is then assembled. Steps s72 through s78 may be performed in any order. It does not matter which pieces are coupled to one another first or if the pieces are locked prior to the next piece being added.

In some embodiments, the patient's anatomy may be such that the patient does not need all three bodies 12, 14, 16. In those cases, two of the bodies 12, 14, 16 may be used in any combination that best fits the patient's anatomy. In other embodiments, the patient's anatomy may require multiple middle bodies 14. In such cases, more than one middle body 14 may be used.

In one embodiment, the bodies 12, 14, 16 are made of a lightweight sterilizable material such as aluminum and the locking mechanisms 22, 56 are made using stainless steel. In other embodiments, the locking mechanisms may also be made of aluminum or other sterilizable material. In other embodiments, the bodies 12, 14, 16 may be made of other sterilizable material. In some embodiments, the trial 10 may be made entirely of plastic.

Although the embodiments above have all been described as forming a distal stem, it should be understood that the invention may include other trials. For example, the same type of locking mechanism could be used with a distal stem connecting to a neck portion of a hip prosthesis. In other embodiments, the distal body 12 could be a broach or other instrument that is attached to a middle body 14 or proximal body 16. Alternatively, the broach could be attached via the locking mechanism described to a neck portion.

While the invention has been illustrated and described in detail in the drawings and foregoing description, such an illustration and description is to be considered as exemplary and not restrictive in character, it being understood that only the preferred embodiment has been shown and described and that all changes and modifications that come within the spirit of the invention are desired to be protected.

There are a plurality of advantages of the present invention arising from the various features of the present invention and associated method described herein. It will be noted that alternative embodiments of the modular trial assembly and associated method of the present invention may not include all of the features described yet still benefit from at least some of the advantages of such features. Those of ordinary skill in the art may readily devise their own implementations of a modular trial assembly and associated method that incorporate one or more of the features of the present invention and fall within the spirit and scope of the present invention as defined by the appended claims.

What is claimed is:

1. A modular prosthetic trial for a joint prosthesis, comprising:
   a first piece having a proximal section and a distal section configured for implantation in a bone, the proximal section having a non-threaded proximally extending protrusion in the form of a pin having a lip;
   a second piece having a proximal section and a distal section, the distal section including a recess for receiving the pin; and
   a locking mechanism at least partially disposed within the recess of the second piece, the locking mechanism sized and shaped to engage the protrusion such that the locking mechanism locks the first piece to the second piece, the locking member includes first and second opposite walls with a recess between the first and second opposite walls through which the pin can extend, at least one of the walls defining a ramp which extends spirally towards an edge of the wall so that, with the locking mechanism in an unlocked position, the pin can be inserted into the recess until the lip has passed the ramp, and so that rotation of the locking mechanism towards a locked position causes the ramp to engage the lip and to draw the pin progressively into the recess to lock the first piece to the second piece.

2. The trial of claim 1, wherein when the locking mechanism is in a locked position, and a thickest portion of the spiral edge engages the lip.

3. The trial of claim 1, wherein said locking mechanism includes an instrument-engagement portion for receiving an instrument.

4. The trial of claim 1, wherein the proximal portion of the second piece includes a non-threaded proximally extending protrusion.

5. The trial of claim 1, further comprising:
   a third piece having a proximal end and a distal end, the distal end including a recess for receiving the non-threaded proximally extending protrusion; and
   a second locking mechanism at least partially disposed within the recess of the third piece, the locking mechanism sized and shaped to engage the protrusion such that the locking mechanism locks the second piece to the third piece.

6. A method for assembling a modular trial comprising:
   using a first piece having a proximal section and a distal section configured for implantation in a bone, the proximal section having a non-threaded proximally extending protrusion in the form of a pin having a lip, a second piece having a proximal section and a distal section, the distal section including a recess for receiving the pin, and a locking mechanism at least partially disposed within the recess of the second piece, the locking mechanism sized and shaped to engage the protrusion such that the locking mechanism locks the first piece to the second piece, the locking member includes first and second opposite walls with a recess between the first and second opposite walls through which the pin can extend, at least one of the walls defining a ramp which extends spirally towards an edge of the wall inserting the pin from the first piece into the corresponding recess in the distal portion of the second piece until the lip has passed the ramp; and rotating the locking mechanism towards a locked position, causing the ramp to engage the lip and to draw the pin progressively into the recess to lock the first piece to the second piece.

7. The method of claim 6, wherein activating the locking mechanism includes using a tool to engage the locking mechanism.

8. A kit for use in performing joint arthroplasty, the kit providing:

a plurality of first trial pieces having a proximal section and a distal section configured for implantation in a bone, the proximal section having a non-threaded proximally extending protrusion in the form of a pin having a lip;

a plurality of second trial pieces having a proximal section and a distal section, the distal section including a recess for receiving the pin and the proximal section including a non-threaded proximally extending protrusion, wherein each of the plurality of second trial pieces includes a locking mechanism at least partially disposed within the recess of the second trial piece, the locking mechanism sized and shaped to engage the protrusion such that the locking mechanism locks the first trial piece to the second trial piece, the locking member includes first and second opposite walls with a recess between the first and second opposite walls through which the pin can extend, at least one of the walls defining a ramp which extends spirally towards an edge of the wall so that, with the locking mechanism in an unlocked position, the pin can be inserted into the recess until the lip has passed the ramp, and so that rotation of the locking mechanism towards a locked position causes the ramp to engage the lip and to draw the pin progressively into the recess to lock the first piece to the second piece;

a third trial piece, the third trial piece including a proximal end and a distal end, the distal end including a recess for receiving the non-threaded proximally extending protrusion of one of the plurality of second trial pieces, the distal end further including a locking mechanism at least partially disposed within the recess of the third trial piece, the locking mechanism sized and shaped to engage the protrusion such that the locking mechanism locks the second trial piece to the third trial piece.

9. The kit of claim 8, wherein each of the plurality of first trial pieces differ from one another in at least one of size and shape.

10. The kit of claim 8, wherein the plurality of second trial pieces differ from one another in size.

11. The kit of claim 8, wherein the locking mechanism of each of the second trial pieces and the locking mechanisms of the third trial piece have the same shape and the non-threaded proximally extending protrusion of each of the plurality of first pieces and the non-threaded proximally extending protrusion of each of the plurality of second pieces also have the same shape such that the third trial piece may be connected to one of the plurality of first trial pieces without one of the plurality of second trial pieces in-between.

12. The kit of claim 8, further comprising a wrench for engaging the locking mechanism of the plurality of second trial pieces and the third trial piece, such that when the wrench is turned, the locking mechanism locks assembled pieces together.

\* \* \* \* \*